United States Patent
Peterson et al.

(10) Patent No.: US 6,235,199 B1
(45) Date of Patent: May 22, 2001

(54) PARALLEL PLUMBING SUPPLY SYSTEM

(75) Inventors: Michael J. Peterson, Nashville; Richard M. Russell, Brentwood, both of TN (US)

(73) Assignee: Dialysis Systems, Inc., Nashville, TN (US)

( * ) Notice: Subject to any disclaimer, the term of this patent is extended or adjusted under 35 U.S.C. 154(b) by 0 days.

(21) Appl. No.: 09/267,977

(22) Filed: Mar. 12, 1999

(51) Int. Cl.[7] .......................... B01D 61/24; B01D 61/28
(52) U.S. Cl. .......................... 210/646; 210/85; 210/97; 210/195.1; 210/195.2; 210/252; 210/253; 210/645; 210/739; 137/599; 137/861
(58) Field of Search .......................... 210/645, 646, 210/647, 739, 85, 97, 195.1, 195.2, 252, 253, 232, 417, 321.65; 137/599, 861

(56) References Cited

U.S. PATENT DOCUMENTS

| | | |
|---|---|---|
| 4,388,184 | 6/1983 | Brous et al. .......................... 210/96.2 |
| 4,477,342 | 10/1984 | Allan et al. .......................... 210/87 |
| 4,596,549 * | 6/1986 | Minami .......................... 604/5 |
| 4,747,822 | 5/1988 | Peabody .......................... 604/29 |
| 4,828,693 | 5/1989 | Lindsay et al. .......................... 210/137 |
| 5,276,611 | 1/1994 | Ghiraldi .......................... 364/413.03 |
| 5,616,248 * | 4/1997 | Schal .......................... 210/647 |
| 5,643,201 | 7/1997 | Peabody et al. .......................... 604/31 |
| 5,792,367 | 8/1998 | Mattisson et al. .......................... 210/741 |
| 5,972,223 * | 10/1999 | Jonsson et al. .......................... 210/647 |

OTHER PUBLICATIONS

Marieb, Human Anatomy & Physiology, $2^{nd}$ Ed., p. 892 (1992) entitled "A Closer Look Renal Failure and the Artificial Kidney". This paper describes basic dialysis technology.

Procedures Nurse's Reference Library Intermed Communications, Inc., p. 619 (1983) entitled "Principles of Hemodialysis".

"Basic System Control and Valve Sizing Procedures", Bulletin No. THE–1165, brochure of ITT (1970).

* cited by examiner

*Primary Examiner*—John Kim
(74) *Attorney, Agent, or Firm*—Waddey & Patterson; Lucian Wayne Beavers

(57) ABSTRACT

The present invention comprises methods and apparatus for biological-processing unit fluid conveyance and pumping systems. The invention teaches methods of reducing fluid flow resistance and reducing pumping requirements for supplying fluid to the biological-processing unit. Some preferred embodiments of the invention are optimized for dialysis machines and dialysis clinics. In some select embodiments the invention is accomplished utilizing two supply legs in fluid parallel communication. A clinic utilizing fluid parallel supply legs has reduced fluid resistance as compared to a clinic utilizing series arranged supply legs. This reduces initial set-up costs, operating costs and time to construct fluid conveyance systems. Other advantages and embodiments are also disclosed.

31 Claims, 10 Drawing Sheets

PARALLEL PLUMBING SUPPLY SYSTEM

BACKGROUND OF THE INVENTION

The present invention relates to a system for plumbing the water supply connections to dialysis machines in a dialysis treatment unit. A system for fluid delivery in a dialysis clinic is discussed in U.S. patent application Ser. No. 09/065,780 filed Apr. 23, 1998, entitled "System for Fluid Delivery in a Dialysis Clinic," which is hereby incorporated herein by reference.

In renal failure, the filtrate formation decreases or stops completely. Nitrogenous waste accumulate quickly in the blood when the tubule cells are not working, a condition called azotemia, and blood pH tumbles to the acidic range. To prevent consequences of azotemia, the blood must be cleansed of metabolic waste and its ionic composition must be adjusted to normal levels by dialysis while the kidneys are shut down. In hemodialysis, which uses an "artificial kidney" apparatus, the patient's blood is passed through a membrane tubing that is permeable only to selected substances, and the tubing is immersed in a bathing solution that differs slightly from normal cleansed plasma.

FIG. 1 shows a prior art renal dialysis apparatus for performing renal dialysis. The apparatus depicted in FIG. 1 includes a cellophane membrane 12 (tubing containing blood). The cellophane or polysulfone membrane 12 is immersed in dialyzing (bathing) solution 14. The patient's blood passes through an arterial bloodline 16 and is pumped through the cellophane membrane 12 with the aid of a blood pump 18. Blood passes through the cellophane membrane 12 through a venous bloodline 20 back to the patient. A bubble trap 22 is positioned between the cellophane membrane 12 and the venous bloodline 20.

Compressed air 24 forces fresh dialyzing solution 26 through the cellophane membrane 12. The fresh dialyzing solution 26 is passed through a constant temperature vat 28 so that it will not adversely effect the temperature of the patient's blood. As fresh dialyzing solution passes into the dialysizer 14 (also referred to as bathing solution 14) used dialyzing solution 30 is passed out.

It is known by those with skill in the art that dialysis treatment is pressure sensitive. To operate properly dialysis machines must generally operate within known parameters. One of the parameters is the pressure of the fresh dialyzing solution 26 applied to the dialysizer 14. The following prior art discusses methods and apparatus for the parameters of dialysis machines: (1) U.S. Pat. No. 5,276,611 by Ghiraldi entitled "Management Of Parameters Relating To A Dialysis Treatment"; (2) U.S. Pat. No. 4,747,822 entitled "Continuous Flow Peritoneal Dialysis System And Method"; (3) U.S. Pat. No. 5,643,201 entitled "Continuous Peritoneal Dialysis Apparatus" by Peabody, et al.; and (4) U.S. Pat. No. 5,792,367 entitled "System And Method For Monitoring A Flow Of Dialysis Fluid In A Dialysis Machine" by Mattisson, et al, whereby these patents are hereby incorporated herein by reference.

To avoid bacterial growth, and satisfy government requirements, it is required that the flow rate through dialysis solution supply piping be no less than three feet per second. FIG. 2 shows a prior art dialysis plumbing system 32 for supplying water or dialysate 34 to a plurality of dialysis machines 36.

In the prior art dialysis plumbing system 32 shown in FIG. 2, the source of dialysate 34 is pumped by a pump 38 through a supply line 40 to the plurality of dialysis machines 36. A return line 42 is connected to the supply line 40. A flow meter 44 is located proximate the dialysate source 34 to monitor the flow rate in the return line 42. If the flow rate measured at the flow meter proximate the source on the return line is not less than three feet per second, then the flow rate through the entire piping will be no less than three feet per second.

In a typical hospital environment, the source 34 may be located hundreds of feet from the actual clinic containing the dialysis machines 36. The clinic itself may be hundreds of feet long. It will be appreciated that the supply line 40 may be many of hundreds of feet long. Thus, in order to maintain a flow rate of three feet per second at the return end 46 of the return conduit (return line) 42, very high pressures may be necessary at the early portion of the supply conduit (supply line) 40 just downstream of the pump 38 (i. e., the front end of the system). This causes considerable difficulties in designing plumbing systems for dialysis clinics. To achieve a 3 fps flow rate at the back end (return end) of the piping layout, prior art techniques require significant pressures at the front end of the system. Thus, the front end of the piping layout drives the pump and piping material and joining strength requirements. This leads to using overpowered and expensive pumps, and overbuilt piping. Operational costs of such over-pressured systems are simultaneously inflated. There have been instances of piping failures of such systems, and instances of damage to equipment. Additionally, pressure reducing devices are often required such that the dialysis machines connected to the early portion of the fluid system are not over-pressured. It is believed that the present invention overcomes these problems.

SUMMARY OF THE INVENTION

The present invention relates to plumbing systems for dialysis machines and overcomes problems associated with prior art plumbing systems for dialysis machines.

The present invention encompasses a biological-processing installation comprising a source for supplying a fluid to a plurality of biological processing units. A pump is located in fluid communication with the source. A fluid supply loop is placed in fluid communication with the pump and the source. The fluid supply loop includes a feeder conduit in fluid communication with the pump, and a plurality of supply legs in parallel fluid flow relative to each other. Each supply leg is in fluid communication with the feeder conduit in at least one of the plurality of biological-processing units. A return conduit is placed in fluid communication with each of the supply legs. The return conduit has a return conduit end in fluid communication with the source.

Another embodiment of the present invention includes a dialysis clinic comprising at least four dialysis machines and a source of water (also referred to herein as dialysate). A pump is positioned in fluid communication with the source, and a feeder conduit is positioned in fluid communication with the pump. Two supply legs are fluidly parallel. Each supply leg is in fluid communication with the feeder conduit and at least two dialysis machines. A return conduit is positioned in fluid communication with each supply leg and the source.

It will be apparent to those with skill in the art that the present invention also includes methods of supplying fluid to a plurality of biological filtering units. One such method comprises the steps of providing a fluid source and communicating fluid in the fluid source to a second plurality of supply legs. The second plurality of supply legs are arranged fluidly parallel relative to each other. The method also includes allowing fluid to flow through the supply legs to a return conduit having a return end in fluid communication with the fluid source. At least one filtering unit is placed in fluid communication with each supply leg.

It is also an object of the present invention to provide a dialysis clinic having reduced flow resistance. One such embodiment comprises a feeder conduit and at least two supply legs in parallel fluid arrangement, wherein each supply leg is in fluid communication with the feeder conduit. At least two dialysis machines are respectively fluidly connected to the at least two supply legs. A return conduit is positioned in fluid communication with the at least two supply legs. Thus, the resistance to fluid flow is reduced as compared to a series arrangement of dialysis machines.

A method of reducing flow resistance through dialysis piping comprises, in one embodiment, the steps of supplying a plurality of dialysis machines and arranging the dialysis machines in parallel fluid communication.

Accordingly it is an object of the present invention to provide means and methods for supplying fluid to bio-equipment at operable pressures.

Another object is to provide fluid at sufficient flow rates and pressures to inhibit bacteria growth in the supply pipes.

A further objective is to provide means and methods for reducing pumping requirements as compared to an equivalent series piping layout. A still further objective is to reduce operating costs as compared to an equivalent series piping layout.

Another objective is to reduce pipe layout front end overbuild, i. e. reduce the need for excessive pipe and joint strength, as compared to the back end of the fluid delivery system.

Another objective is to provide means and methods for reducing flow resistance in supply pipes.

Another objective is to reduce the risk of catastrophic pipe failure or damaging bio-equipment by supplying fluids at excessive pressures.

Another objective is to eliminate the need to install pressure regulating devices at connections between the fluid delivery system and bio-equipment needed in the prior art to prevent over pressurization and possible damage to said bio-equipment.

Another objective of the present invention is to provide means and methods for reducing locations in supply piping conducive to bacteria growth. A further objective is to reduce bacteria by utilizing pipe which is hydraulically smoother, minimizes joints and has fewer solvent welded connections, as compared to standard current art pvc piping. A further objective is to reduce the area on which bacteria may grow by utilizing pipe having a smaller diameter than standard pipe used in the prior art. A further objective is to reduce the number of locations in which bacteria may grow by requiring fewer fittings and couplers as compared to conventional piping. A further objective is to require fewer fittings by utilizing flexible tubing for the pipe.

Another objective of the present invention is to provide means and methods for adjusting the flow to bio-equipment. A further objective is to provide means for balancing the flow to the bio-equipment while minimizing the need for balancing devices. A further objective is to provide means for adjusting as well as balancing the pressures in the supply lines.

Another objective is to provide a mobile dialysis clinic. A further objective is to provide means and methods for providing dialysate treatment at reduced costs. A further objective is to provide means and methods for reducing the operating costs of a dialysis clinic.

Another objective is to reduce the overall first cost of a dialysis fluid delivery system and therefore clinic.

Another objective is reduce the overall maintenance costs of a dialysis fluid delivery system.

Another objective is to provide a highly flexible fluid delivery system which reduces the requirements for existing buildings to be retrofitted into dialysis clinics.

Another objective is to provide a fluid delivery system which by nature of its design may be constructed in very little time allowing for more rapid construction of needed clinics.

Another objective is to provide a fluid delivery system which may be quickly, easily, temporarily installed in a natural or man-made disaster.

Other objects and advantages of the present invention will be apparent to those with skill in the art from the teachings disclosed herein including the attached drawings and claims.

DESCRIPTION OF THE PREFERRED EMBODIMENTS

Figure 1:
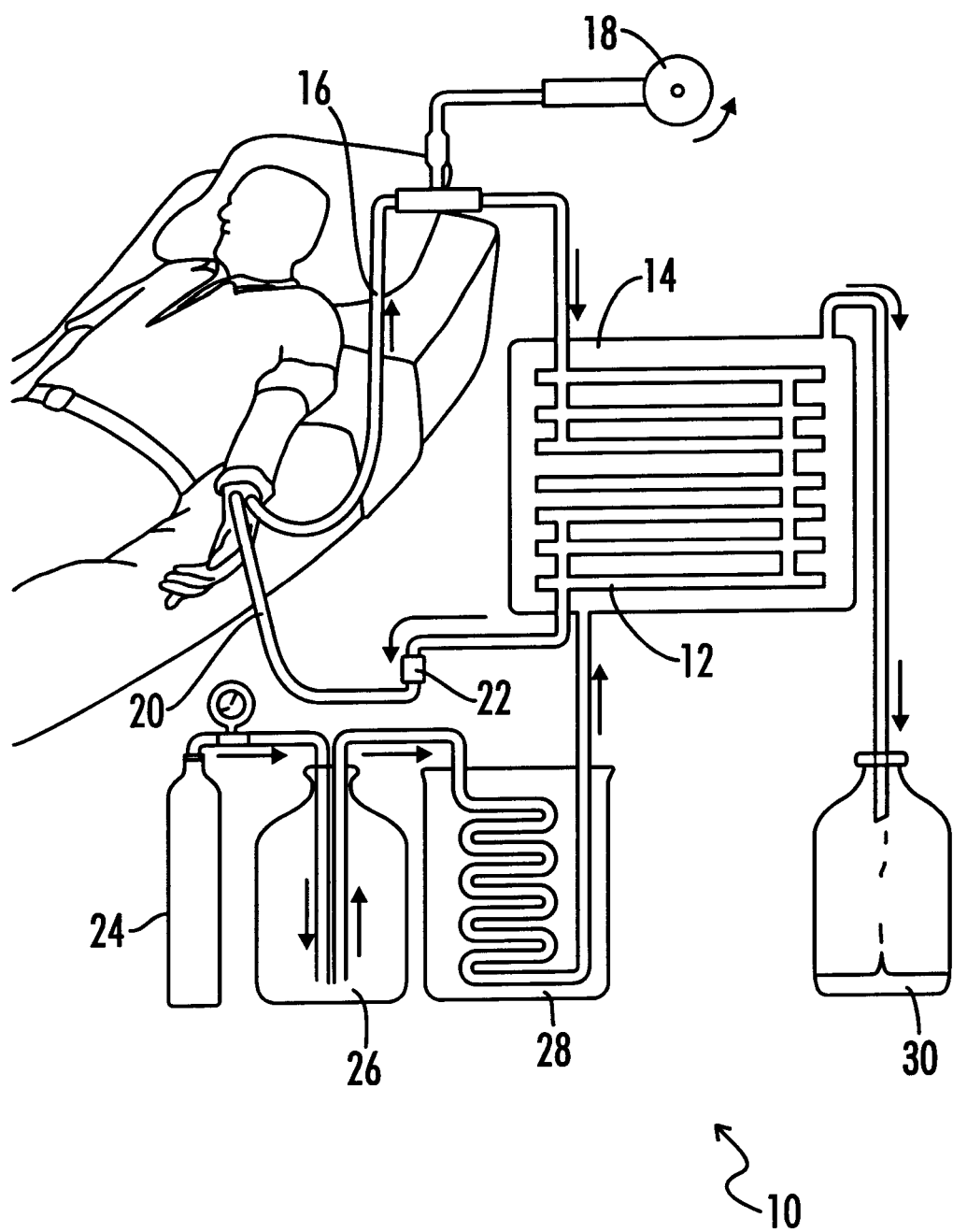
FIG. 1 shows a prior art schematic representation of a renal dialysis apparatus.

The present invention relates to plumbing systems for biological-processing units. Particular embodiments are optimized for plumbing the water supply connections into the dialysis machines in a dialysis clinic. The present invention will be best understood from the following description of exemplary embodiments with reference to the attached drawings, wherein like reference numerals refer to like parts.

The present invention proposes a modification of the supply conduit.

The discharge from the pump goes to an initial supply conduit portion which splits at a T into two parallel supply lines. Each supply line will flow past only a portion of the dialysis machines. The two supply lines will then rejoin at a T into a common return line.

Each of the parallel supply conduit portions will preferably have valves located just prior to the return T. Similarly, each of the parallel flow conduits may have flow meters located near their end portions to allow flow rates to be monitored. By use of valves, the pressures within the two parallel supply conduits may be balanced if necessary to maintain approximately equal flow rates through each of those conduits.

By the system just described, the same number of dialysis machines can be supplied, while at the same time greatly reducing the resistance to fluid flow provided by those portions of the supply conduit flowing past the dialysis machines. By splitting a given total flow rate between two parallel conduits the resistance to flow is greatly decreased.

By reducing the resistance to fluid flow, smaller horsepower pumps may be utilized thus reducing initial capital costs and also reducing power requirements for operation of the system.

Figure 3:
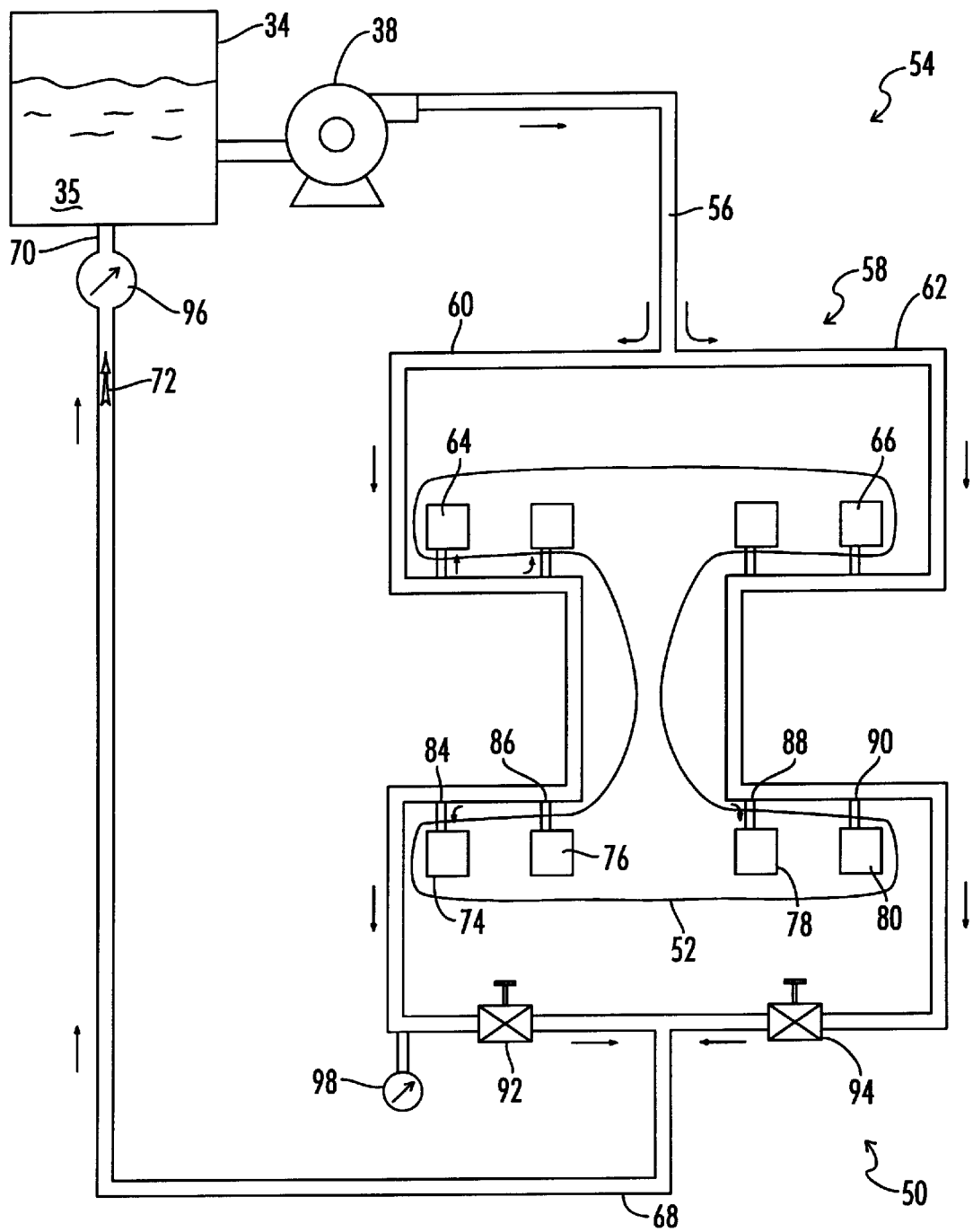
FIG. 3 depicts one preferred embodiment of a plumbing system according to the present invention. Fluid supply legs are arranged in fluid parallelism in FIG. 3.

FIG. 3 shows a biological-processing installation 50 according to an embodiment on the present invention. The biological-processing installation 50 comprises a source 34 for supplying a fluid to a plurality of biological-processing units 52. A pump 38 is positioned in fluid communication with the source 34, a fluid supply loop 54 is in fluid communication with the pump 38 and the source 34. The fluid supply loop 54 includes a feeder conduit 56 in fluid communication with the pump. A plurality of supply legs 58 is in parallel fluid flow relative to each other. Each supply leg, 60 and 62, is in fluid communication with the feeder conduit 56 and at least one of the plurality of biological-processing units, 64 and 66, respectively. A return conduit 68 is in fluid communication with each of the supply legs 58. The return conduit has a return conduit end 70 in fluid communication with the source 34.

The term biological-processing installation, as used herein, is intended to encompass health care facilities, clean room environments, and the pharmaceutical industry. Examples of health care facilities include dental clinics and dialysis clinics. Clean room environments include surgery and emergency rooms. Other facilities commensurate with the use of biological-processing installation herein will be apparent to those of skill in the art. Likewise, biological filter unit and biological processing unit are intended to encompass biomedical equipment used in biological-processing installations. Specific embodiments are selected for use with dialysis machines; other specific uses for bio-equipment include providing injectable ultra pure water (also referred to as ISP).

In one embodiment, the fluid 35 has a flow rate 72 at the return conduit end 70 at least as great as a predetermined flow rate. In one preferred embodiment the predetermined flow rate is three feet per second. In some preferred embodiments the biological-processing units 52 are dialysis machines and the fluid 35 includes water.

In a preferred embodiment of the installation 50, the plurality of biological-processing units 52 are dialysis machines, and at least two dialysis machines are in fluid communication with each supply leg. Referring to FIG. 3 dialysis machines 74 and 76 are in fluid communication with supply leg 60 and dialysis machines 78 and 80 are in fluid communication with supply leg 62.

Figure 4:
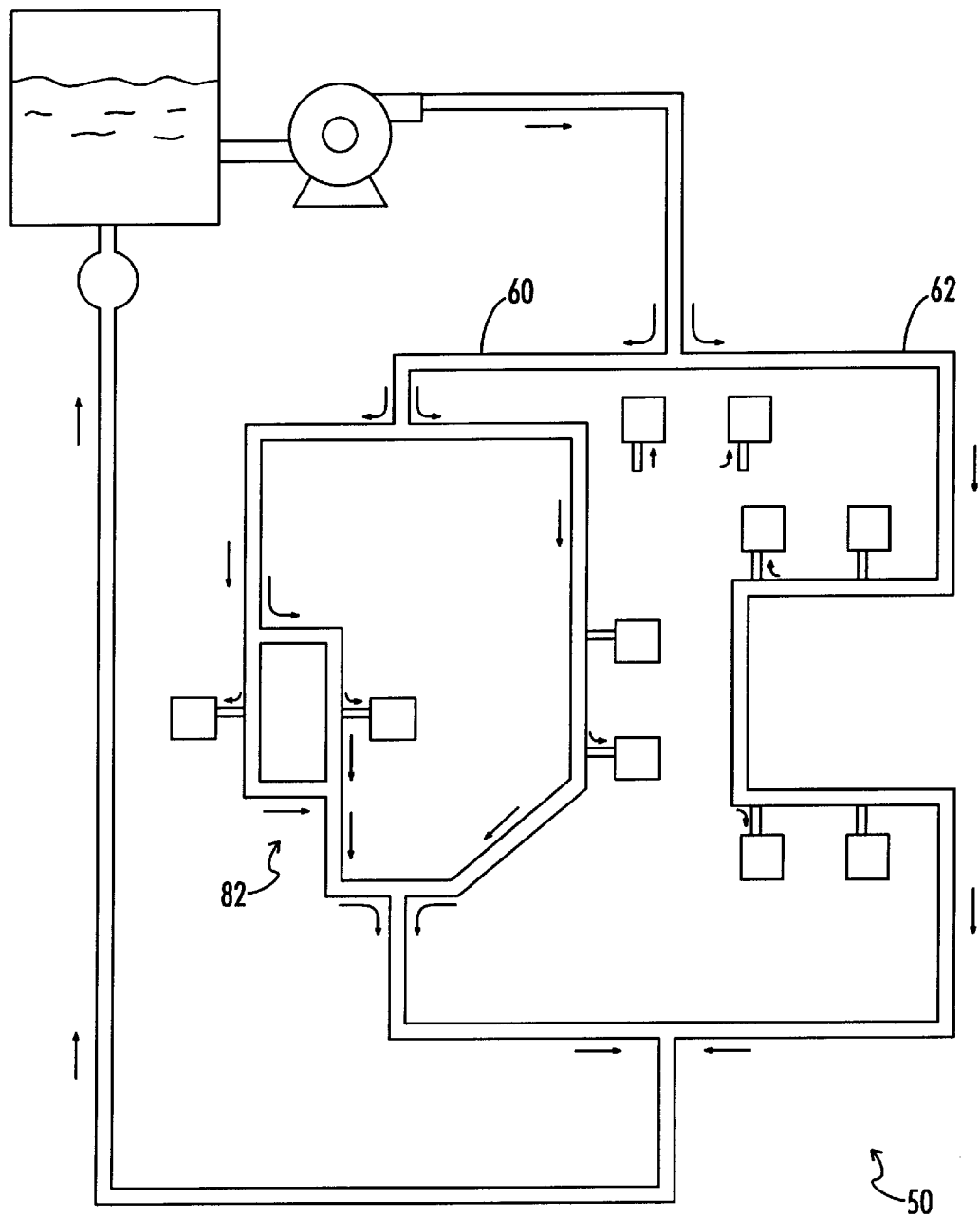
FIG. 4 is a plumbing system similar to that shown in FIG. 3. However, the system shown in FIG. 4 comprises parallel sub-supply legs.

Referring to FIG. 4, the supply leg 60 comprises a plurality of sub-supply legs 82 in parallel fluid flow.

In one preferred embodiment at least two dialysis machines, designated 74 and 76, and 78 and 80 in FIG. 3, are located at respective at least two locations, designated 84 and 86, and 88 and 90, respectively along each supply leg 60 and 62. The at least two locations 84 and 86 along supply leg 60 are in series fluid flow relative to each other.

In a preferred embodiment of the installation 50, at least one of the supply legs comprises an adjustable flow valve 92. In the embodiment shown in FIG. 3 each supply leg, 60 and 62 comprises an adjustable flow valve 90 and 94, respectively and a flow meter 96. In another preferred embodiment at least one of the supply legs 60 comprises a flow meter 98. In one preferred embodiment, the flow meter 98 is a rotometer.

Figure 5:
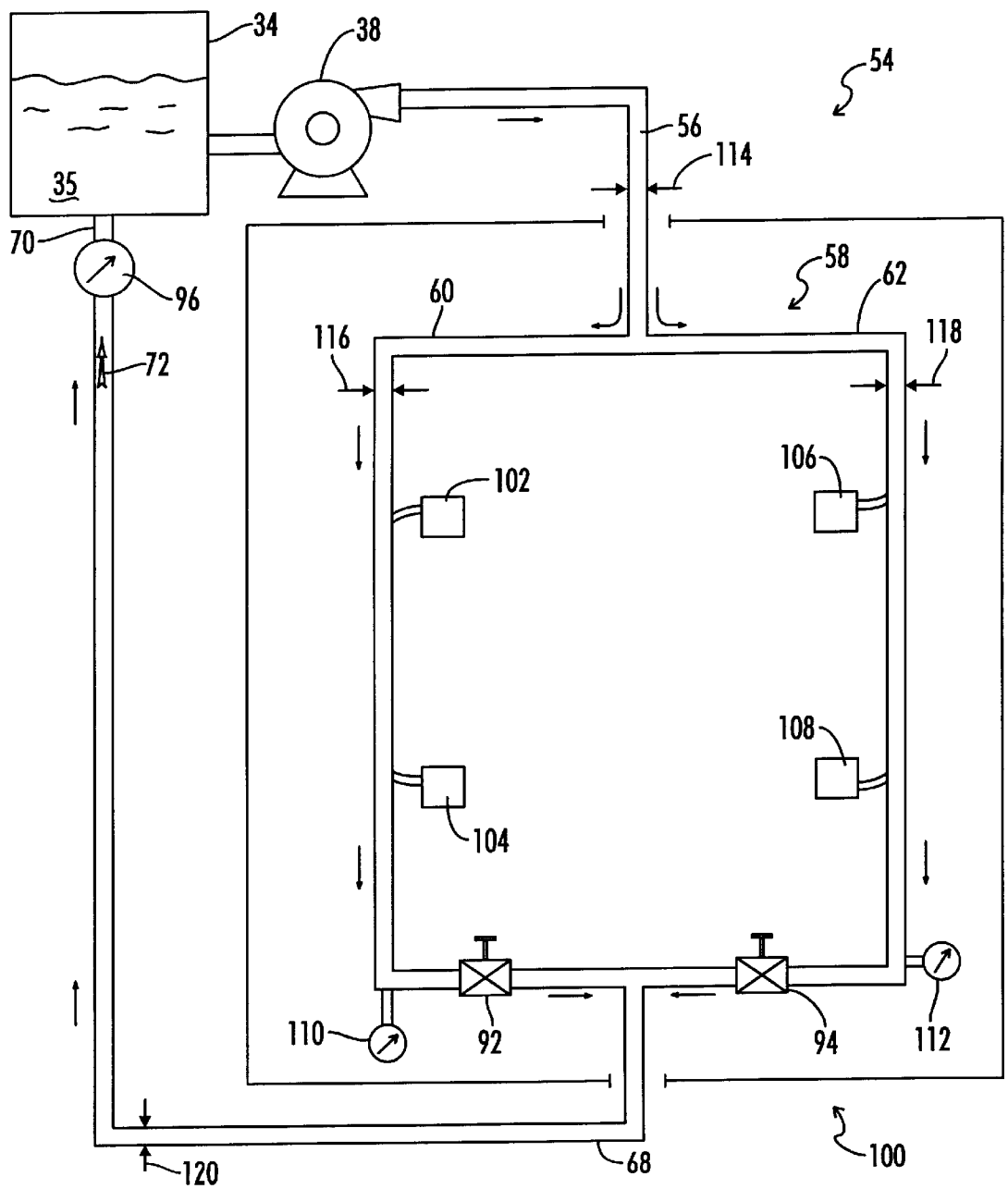
FIG. 5 depicts a dialysis clinic arranged according to an embodiment of the present invention. Parallel supply legs are fluidly connected to dialysis machines. The fluid flow is reduced through the parallel supply legs as compared to the series arranged supply legs in FIG. 2.

FIG. 5 shows another embodiment of the present invention for a dialysis lo clinic 100. The dialysis clinic 100 comprises at least four dialysis machines, designated 102, 104, 106, and 108. A pump 38 is in fluid communication with a source 34 of water (or dialysate) 35. A feeder conduit 56 is in fluid communication with the pump 38. Two supply legs 60 and 62 are fluidly parallel, wherein each supply leg 60 and 62 is in fluid communication with the feeder conduit 56 and at least two dialysis machines 102 and 104, and 106 and 108, respectively. A return conduit 68 is in fluid communication with each leg 60 and 62 and the source 34.

In one preferred embodiment of the clinic 100, each supply leg 60 and 62 comprises a flow meter 110 and 112 respectively and an adjustable flow valve 92 and 94, respectively.

In another embodiment the feeder conduit has a feeder diameter 114. Each supply leg 60 and 62 has a respective supply leg diameter 116 and 118. In select embodiments each respective supply leg diameter 116 and 118 is at least as small as the feeder diameter 114. In some embodiments the return conduit 68 has a return diameter 120 at least as small as one of the respective supply diameters 116 or 118. In some embodiments the return diameter 120 is smaller than the feeder diameter 114.

It will be apparent to those with skill in the art that the present invention also comprises a method of supplying fluid to a plurality of biological units. Referring to FIG. 3, one such method comprises the step of providing a fluid source 34 and communicating fluid 35 in the fluid source 34 to a plurality of supply legs 58. The method includes arranging the plurality of supply legs 58 in fluid parallelism relative to each other and allowing fluid 35 to flow through the supply legs 58 to a return conduit 68 having a return end 70 in fluid communication with the fluid source 34. The method includes providing a plurality of biological filtering units 52 and placing at least one filtering unit 64 and 66 in fluid communication with each supply leg 60 and 62, respectively.

In some embodiments the method comprises the step of maintaining a fluid flow rate 72 at the return end 70 of the return conduit 68 above a predetermined fluid flow rate. In some preferred embodiments the biological filtering units are dialysis machines and the fluid includes water. Preferably the method comprises the step of pumping fluid 35 to the supply legs 58 at non-damaging pressures. Typically, the method comprises the step of balancing respective pressures in the supply legs relative to each other.

Generally, the method of supplying fluid comprises the step of regulating respective pressures in the supply legs within predetermined operable parameters. The predetermined operable parameters are determined such that the biological filtering units 52 are operable. Preferably the method comprises the step of monitoring the flow rate in at least one supply leg. Typically this is done utilizing a flow meter 96 to monitor the flow rate in the supply leg 60.

Generally, the method comprises the step of adjusting a flow valve 92 in at least one supply leg 60. Typically the step of adjusting is done with a step of monitoring a flow rate in each supply leg.

Figure 2:
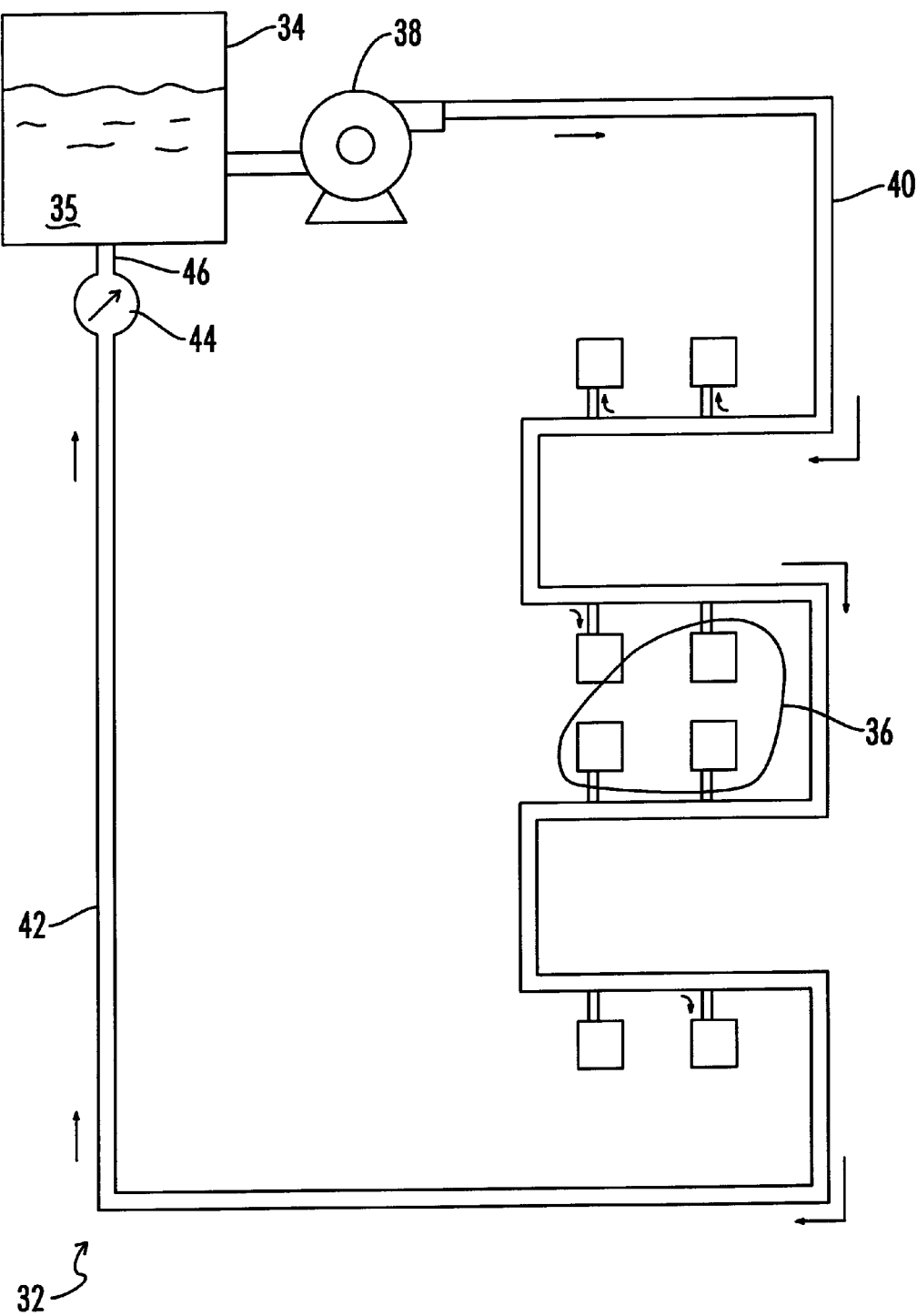
FIG. 2 shows a prior art dialysis clinic. The dialysis machines are arranged in a series connection.

The present invention encompasses a clinic 100 having a reduced fluid flow resistance. The clinic 100 includes a feeder conduit 56 and at least two supply legs 60 and 62 in fluid arrangement. Each supply leg 60 and 62 is in fluid communication with the feeder conduit 56. At least two dialysis machines 102 and 104, 106 and 108 are respectively fluidly connected to the at least two supply legs 60 and 62. A return conduit is placed in fluid communication with the at least two supply legs 60 and 62. Thus, the resistance to fluid flow is reduced as compared to a series arrangement of dialysis machines. A series arrangement of dialysis machines is shown in FIG. 2. The arrangement shown in FIG. 2 is a serpentine series arrangement.

In some preferred embodiments each supply leg 60 and 62 comprises four dialysis machines, including one of the at least two dialysis machines 102 and 106. The parallel fluid arrangement of all the dialysis machines is such that the resistance to fluid flow is reduced as compared to a series arrangement of all the dialysis machines.

It will be apparent to those with skill in the art that the present invention also encompasses a clinic wherein the parallel fluid arrangement is such that pumping horsepower requirements are reduced as compared to pumping horsepower requirements for a series arrangement of the at least two dialysis machines.

Accordingly, the present invention also includes a method of reducing flow resistance through dialysis piping comprising the steps of supplying a plurality of dialysis machines and arranging the dialysis machines in parallel fluid communication. Preferably the step of arranging the dialysis machines comprises arranging four dialysis machines on two supply legs, wherein the supply legs are in parallel fluid communication.

Another embodiment of the invention is the method of reducing flow resistance which comprises the step of reducing pumping requirements for parallel arranged dialysis machines as compared to series arranged dialysis machines.

Figure 6:
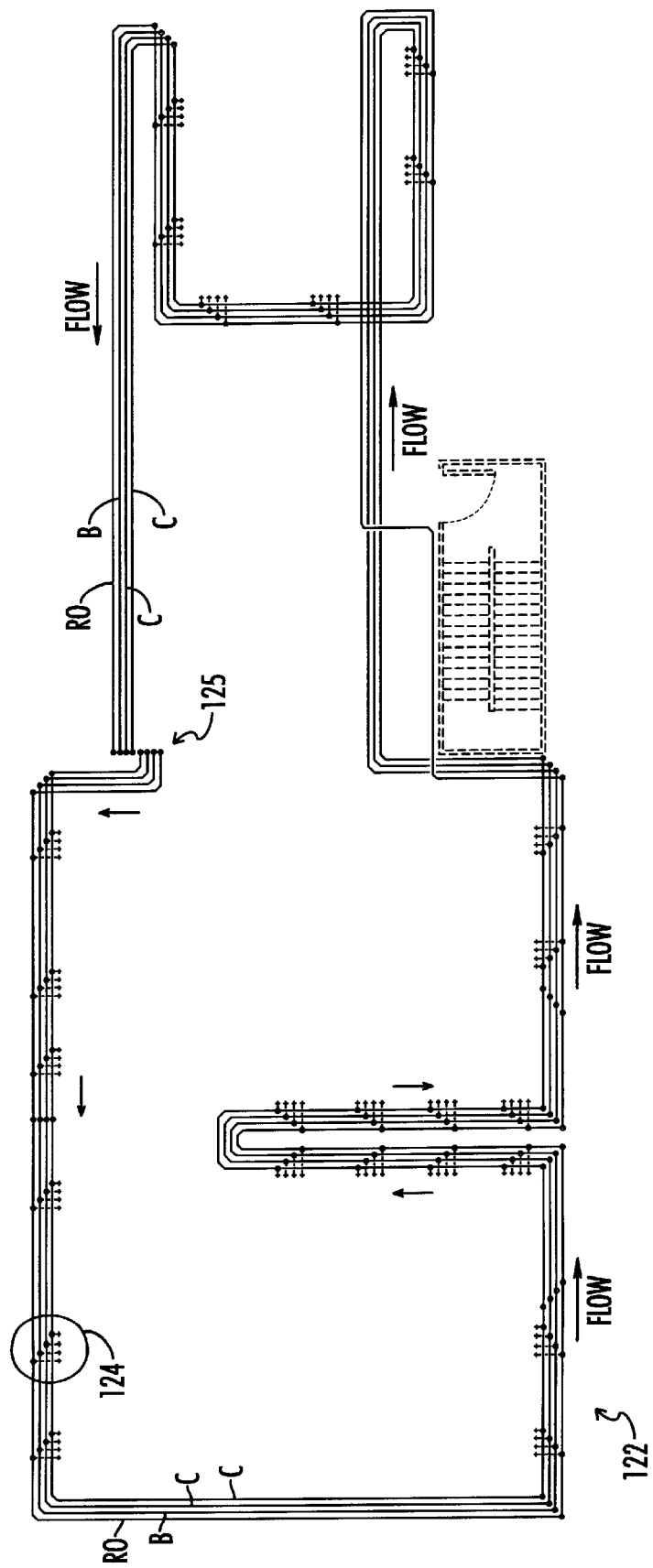
FIG. 6 shows a prior art series supplied 24 unit clinic pipe layout.

At this point it will be useful to discuss an example. The example includes supplying a 24 unit (dialysis machine) clinic. FIG. 6 shows a prior art series supply pipe for a 24 unit clinic 122. The piping layout 122 shown in FIG. 6 comprises 24 stations for hooking into 24 dialysis machines. One representative station is indicated by reference numeral 124. The fluid supply comes up from the basement near location 125, flows through the pipes, and returns to the basement near location 125. The pipe layout 122 shows four pipes for the series. One for permeate (water), two for concentrate, and one for bicarbonate.

The prior art system requires 748 feet of linear pipe plus 143.7 feet of fittings for an approximate equivalent total length of 892 feet. The system must maintain 3 fps flow rate in the loop (a single loop). To maintain this velocity requires a base flow of 5 gallons per minute (gpm) for a ¾" pipe, and 8gpm for 1" pipe.

The machine demand at maximum is 1 liter/min–machine, plus reuse machine. Thus, 24 stations, plus 1 self care equals 25 liters; plus 5 reuse machines at 2 liters/machine equals 10 liters; for a total of 35 liters/min. Or approximately 9.25 gpm. Adding the maximum demand to the base demand yields 14.25 gpm for a ¾" pipe and 17.25 gpm for a 1" pipe.

Pressure loss for a ¾" pipe at 14.25 is 30'/100', and 6'/100' at 5 gpm; for a 1" pipe at 17.25 gpm is 19'/100', and 5'/100' at 8 gpm. Thus, max pressure loss for the ¾" pipe (at 30'/100' for 892' of pipe) is 267 ft/HD. Because the system is open and there is a change in elevation for the source located in the basement, additional head of approximately 20' should be added to yield 287 ft/HD. This requires approximately 125 psi. Similar calculations for the 1" pipe yields 82 psi.

To maintain, or rather compensate for, the above pressure loss requires a pump of approximately 5 Hp with an annual operating cost of approximately $1700 (assuming $0.10 kwhr at 8760 hrs/yr).

It is also worth noting that the above described system includes approximately 144 feet of fittings. Since the bacteria is most likely to grow in grooves, which are particularly prevalent around fittings, another object of the present invention is to reduce the number of fittings required.

Figure 7A:
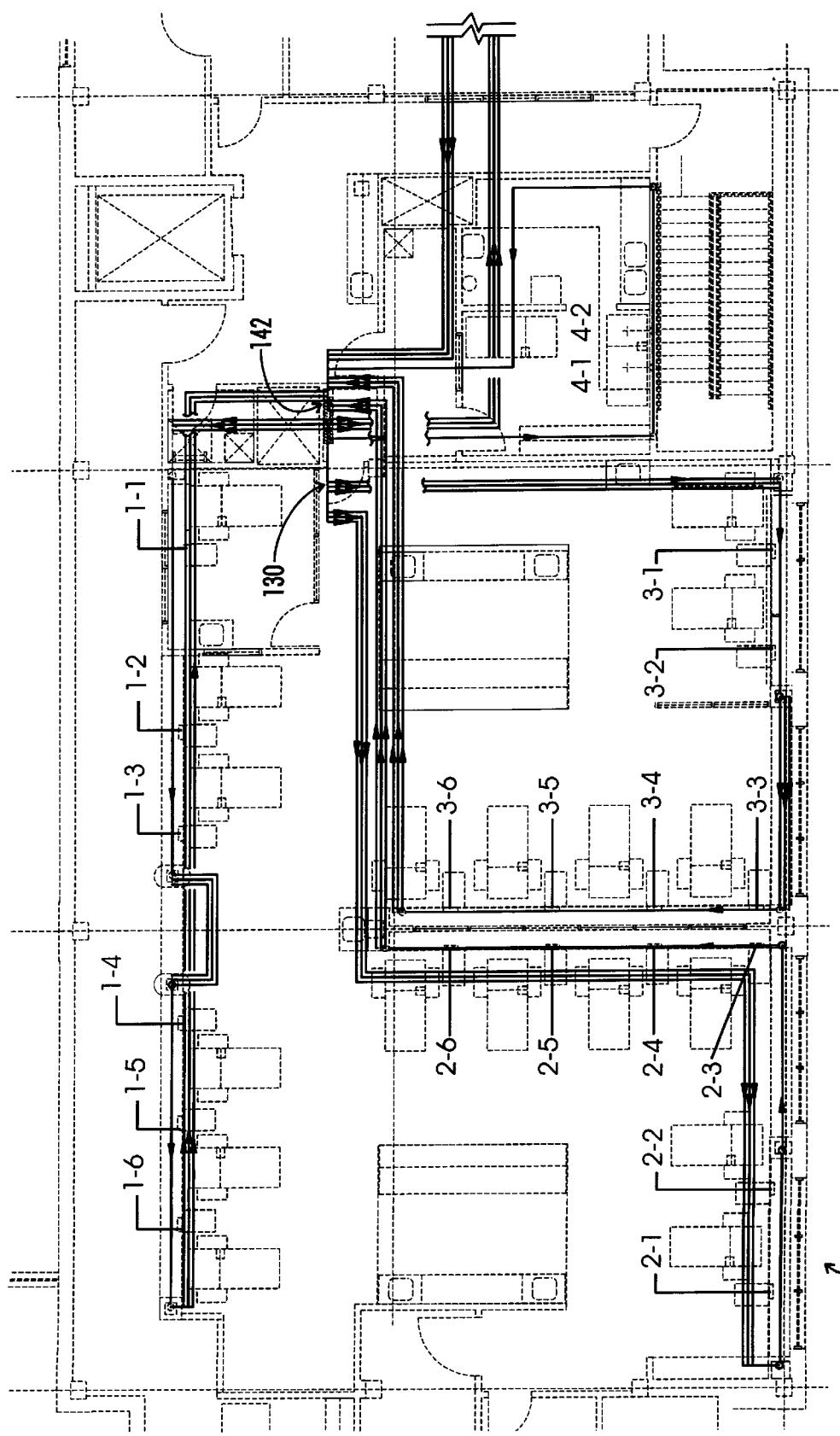
FIGS. 7A and 7B show a plan view of a parallel pipe layout with 5 loops for supplying a 24 unit clinic.
Figure 7B:
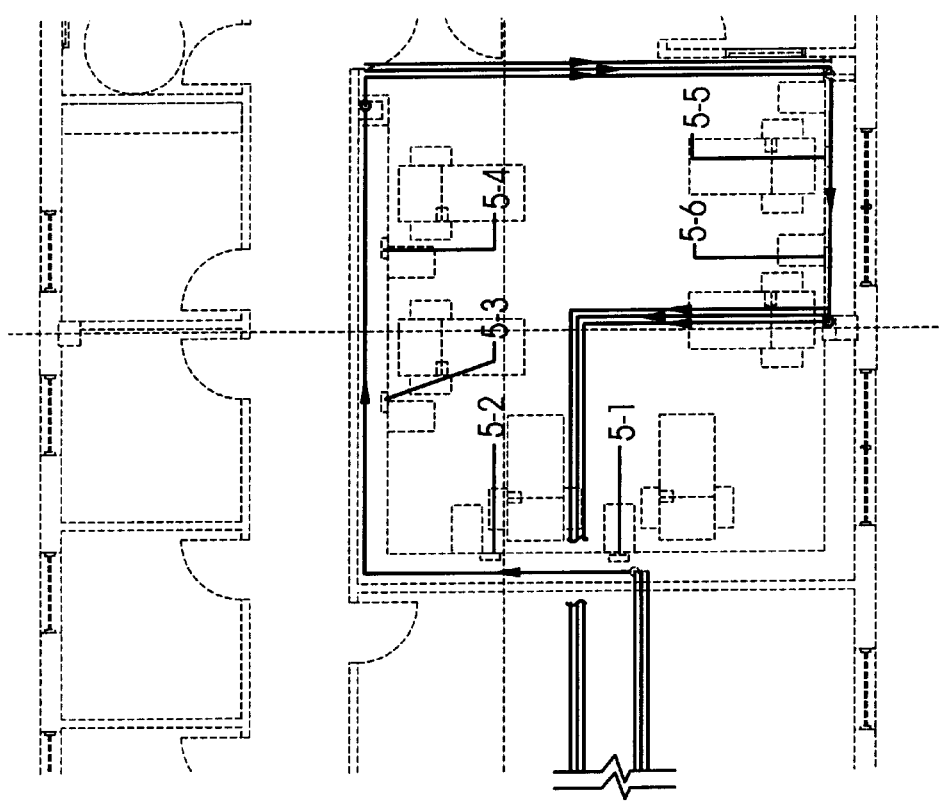
Figure 8:
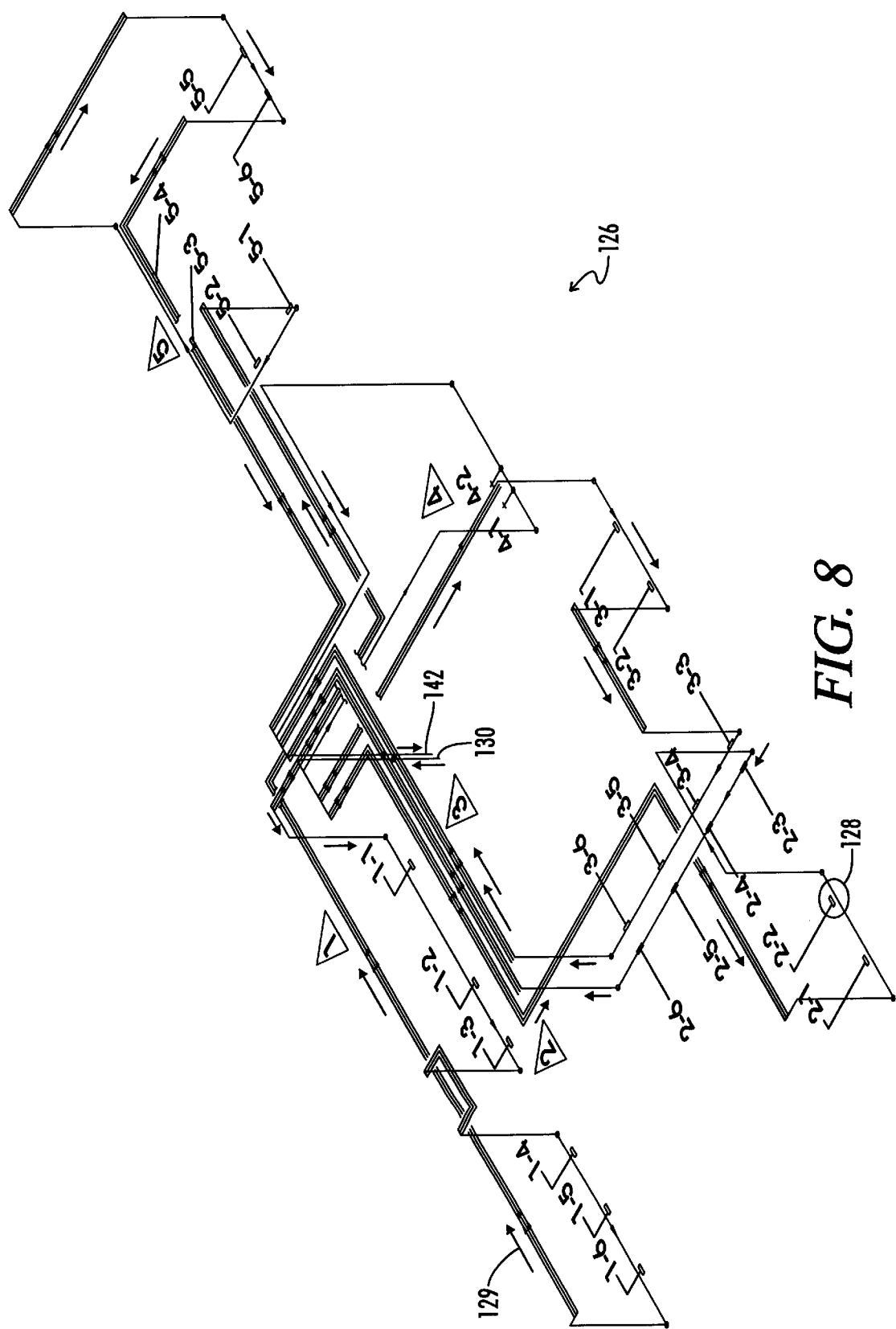
FIG. 8 shows a perspective view of the pipe layout shown in FIG. 7.

FIGS. 7A and 7B show a plan view of an embodiment of a five loop pipe layout 126, according to the present invention, for supplying the same 24 unit clinic embodied in FIG. 6. FIGS. 7A and 7B are joined at the break lines shown on their right and left sides, respectively. FIG. 8 shows a perspective view of the pipe layout 126 shown in FIGS. 7A and 7B. The pipe layout 126 utilizes 5 loops indicated by triangle enclosed loop numbers. Four loops serve fluid to 6 units each. The reuse station receives its own loop (loop number 4) because it has such a large fluid demand as compared to the dialysis machines. Each station is designated by an x-y number, where x is the loop and y is the unit on that loop. Representative station 128 is the second unit on loop 2. The four dialysis machine loops have lengths of 222', 286', 227', and 282' feet. The reuse has a length of 150'. Generally, it is preferred to equalize the lengths of the unit loops to facilitate balancing the system. Flow valves, preferably needle valves, are used to further balance the system. The total equivalent lengths for the loops, including fittings are: 235', 313', 239', 156', and 294'. Loop 4 is the reuse loop. Flow direction is indicated by arrows 129. Height changes are typically necessary for laying pipe around doors and such.

Figure 9:
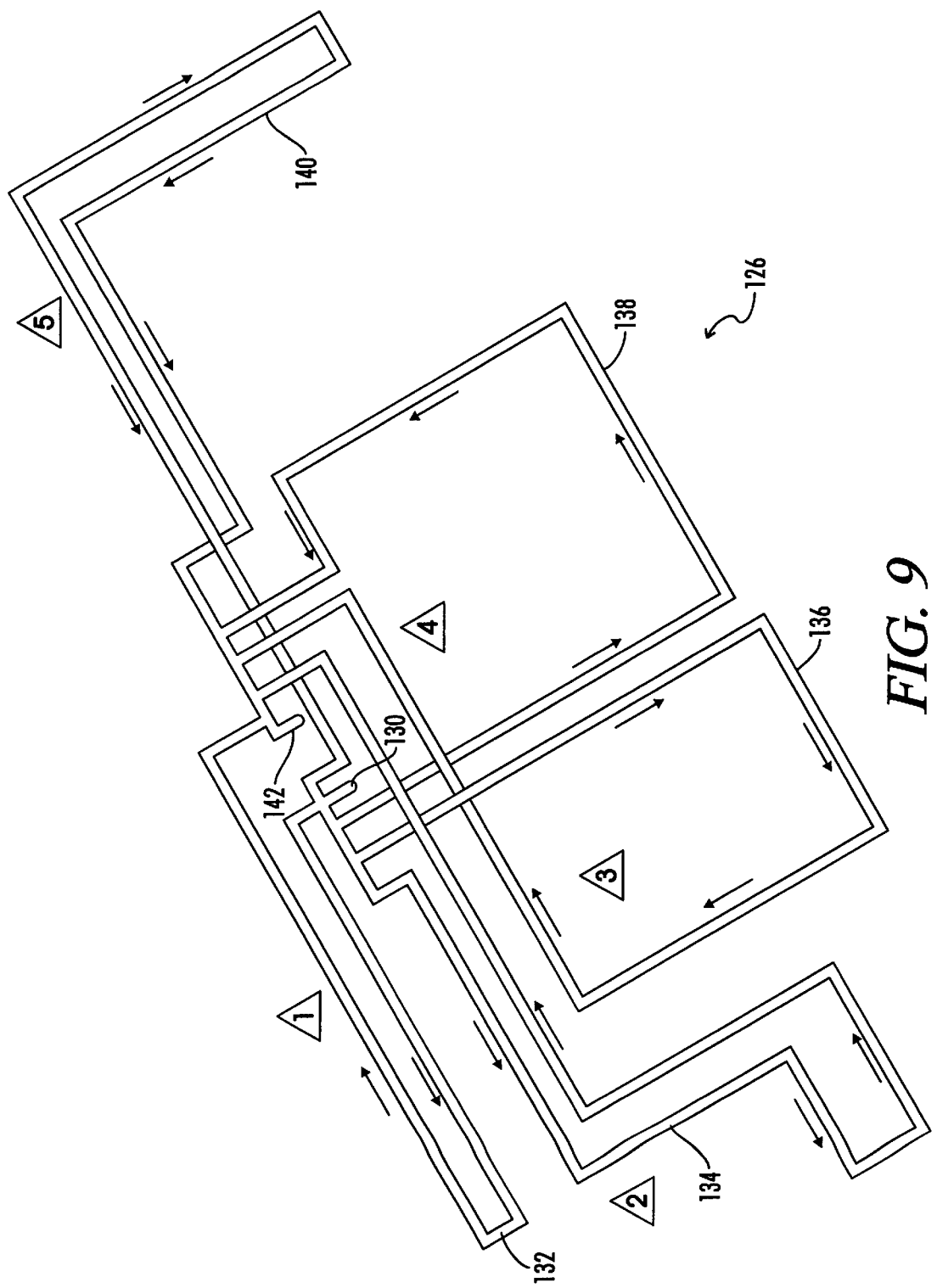
FIG. 9 shows a simplified view of the pipe layout shown in FIG. 8.

FIG. 9 shows a simplified view of the pipe layout 126 shown in FIGS. 7A and 7B and 8. The supply from the basement 130 supplies fluid through the first loop 132, the second loop 134, the third loop 136, the fourth loop 138, and the fifth loop 140. The fluid circulates through the loops 132–140, at a flow rate greater than 3 fps, and returns to the basement through the basement return 142.

It will be appreciated that each of the "loops" shown in FIGS. 7, 8 and 9 in fact includes three or more parallel loops carrying water, one or more additives and bicarbonate to the dialysis machine.

To maintain 3 fps flow rate in ½" tubing requires 2 gpm. Note, that the present invention provides the ability to use smaller diameter pipes because the pressures required to achieve 3 fps will not be as high. Some preferred materials for the pipes are high density cross linked polyethylene, polypropylene, PVDF, polytetrafluoroethylene (sold under the name Teflon®), and stainless steel. Also, in keeping with the concept of reducing fittings and grooves in which bacteria may grow, interconnect fluid conveyances from fluid sources to horizontal treatment chases are formed with continuous tubing allowing long radius bends instead of fitting cells. Preferably the minimum tubing bend radius will be no less than 6 inches.

The machine demand for each loop is as follows:
Loops 1, 2, 3, and 5: 6 units at 1 liter/min÷3.785 1/g =1.56 gpm each;
Loop 4: 5 reuse units at 2 liter/min=2.64 gpm.

Thus, the gpm at max demand for loops 1, 2, 3, and 5 is 3.56 gpm (2 gpm base for ½" tubing plus 1.56 gpm max load); and for loop 4 is 4.56 gpm (2 gpm plus 2.56 gpm max load). The loss/100' for loops 1, 2, 3, and 5, at 3.56 gpm, is 14'/100'; the loss for loop 4 is 20'/100'. Multiplying the equivalent lengths for each loop (1: 235', 2: 313', 3: 239', 4: 156', 5: 294') times the loss per length yields the following required head for each loop:

1: 32.9'+20'=53 ft/23 psi
2: 43.8'+20'=64 ft/28 psi
3: 33.5+20'=54 ft/23 psi
4: 31.2+20'=51 ft/22 psi
5: 41'+20'=61 ft/27 psi.

(20' was added to account for the elevation change from the basement to the clinic since an open system is used in this example.) Thus, a conservative maximum pressure to be supplied is 30 psi (equivalent to 69 ft of head) at 20 gpm.

A pump of approximately 1.5 Hp is required to provide 30 psi (69 ft of head) at 20 gpm. The operating costs at 20 gpm is approximately $903 per annum; at 18 gpm is approximately $751 per annum.

The pressures and pump requirements for the parallel loop design are significantly less than those for a conventional series loop. Note that pressures in excess of 5–10 psi at a dialysis machine can damage it. The use of quick connects provides further protection because there is a pressure drop across the quick connect, in most cases. The prior art requires regulating pressure values at the front end of the system to avoid feeding the machines at too high of a pressure. These concerns are largely minimized if not entirely reduced or eliminated in the present invention.

The above loop, or parallel pipe, example is also exemplary of one preferred embodiment. The embodiment utilizes 6 units per loop, with each loop having a length between 200 to 300 feet.

Thus, although there have been described particular embodiments of the present invention of a new and useful Parallel Plumbing Supply System, it is not intended that such references be construed as limitations upon the scope of this invention except as set forth in the following claims.

What is claimed is:

1. A biological-processing installation comprising:
   a source for supplying a fluid including water to a plurality of dialysis machines;
   a pump in fluid communication with the source; and
   a fluid supply loop in fluid communication with the pump and the source, the fluid supply loop including,
   a feeder conduit in fluid communication with the pump,
   a plurality of supply legs in parallel fluid flow relative to each other, wherein each supply leg is in fluid communication with the feeder conduit and at least one of the plurality of dialysis machines, and
   a return conduit in fluid communication with each of the supply legs, the return conduit having a return conduit end in fluid communication with the source.

2. The installation of claim 1, wherein the fluid has a flow rate at the return conduit end at least as great as a predetermined flow rate.

3. The installation of claim 2, wherein the predetermined flow rate is three feet per second.

4. The installation of claim 1, wherein the plurality of dialysis machines comprises at least two dialysis machines in fluid communication with each supply leg.

5. The installation of claim 4, wherein at least one of the supply legs comprises a plurality of sub-supply legs in parallel fluid flow.

6. The installation of claim 4, wherein the at least two dialysis machines are located at respective at least two locations along each supply leg, wherein the at least two locations along each supply leg are in series fluid flow relative each other.

7. The installation of claim 1, wherein at least one of the supply legs comprises an adjustable flow valve.

8. The installation of claim 1, wherein each supply leg comprises an adjustable flow valve and a flow meter.

9. The installation of claim 1, wherein at least one of the supply legs comprises a flow meter.

10. A dialysis clinic comprising:
    at least four dialysis machines;
    a source of water;
    a pump in fluid communication with the source;
    a feeder conduit in fluid communication with the pump;
    two supply legs fluidly parallel, each supply leg being in fluid communication with the feeder conduit and at least two dialysis machines; and
    a return conduit in fluid communication with each supply leg and the source.

11. The clinic of claim 10, wherein each supply leg comprises a flow meter and an adjustable flow valve.

12. The clinic of claim 10, wherein:
    the feeder conduit has a feeder diameter; and
    each supply leg has a respective supply leg diameter, wherein each respective supply leg diameter is at least as small as the feeder diameter.

13. The clinic of claim 12, wherein the return conduit has a return diameter and the return diameter is smaller than the feeder diameter.

14. A method of supplying fluid to a plurality biological filtering units comprising the steps of:
    providing a fluid source;
    communicating fluid in the fluid source to a plurality of supply legs;
    arranging the plurality of supply legs in fluid parallelism relative to each other;
    allowing fluid to flow through the supply legs to a return conduit having a return end in fluid communication with the fluid source;
    providing the plurality of biological filtering units; and
    placing at least one filtering unit in fluid communication with each supply leg.

15. The method of claim 14, comprising the step of maintaining a fluid flow rate at the return end of the return conduit above a predetermined fluid flow rate.

16. The method of claim 15, wherein the biological filtering units are dialysis machines and the fluid includes water.

17. The method of claim 15, comprising the step of pumping fluid to the supply legs at non-damaging pressures.

18. The method of claim 17, comprising the step of balancing respective pressures in the supply legs relative to each other.

19. The method of claim 14, comprising the step of balancing respective pressures in the supply legs relative to each other.

20. The method of claim 14, comprising the step of regulating respective pressures in the supply legs within predetermined operable parameters, wherein the predetermined operable parameters are determined such that the biological filtering units are operable.

21. The method of claim 14, comprising the step of monitoring the flow rate in at least one supply leg.

22. The method of claim 21, comprising the step of utilizing a flow meter to monitor the flow rate.

23. The method of claim 21, comprising the step of adjusting a flow valve in at least one supply leg.

24. The method of claim 23, comprising the steps of:
monitoring a flow rate in each supply leg; and
adjusting a flow valve in each supply leg.

25. The method of claim 14, wherein the biological filtering units are dialysis machines; and the fluid includes water.

26. A dialysis clinic having reduced fluid flow resistance comprising:
a source of fluid;
a feeder conduit fluidly connected to the source;
at least two supply legs in parallel fluid arrangement, each supply leg being in fluid communication with the feeder conduit;
at least two dialysis machines respectively fluidly connected to the at least two supply legs; and
a return conduit in fluid communication with the at least two supply legs and with the source, whereby
the resistance to fluid flow is reduced as compared to a series arrangement of dialysis machines.

27. The clinic of claim 26, wherein each supply leg comprises four dialysis machines, including one of the at least two dialysis machines, and wherein the parallel fluid arrangement of all of the dialysis machines is such that the resistance to fluid flow is reduced as compared to a series arrangement of all of the dialysis machines.

28. The clinic of claim 26, wherein the parallel fluid arrangement is such that pumping horsepower requirements are reduced as compared to pumping horsepower requirements for a series arrangement of the at least two dialysis machines.

29. A method of reducing flow resistance through dialysis piping comprising the steps of:
supplying at least four dialysis machines; and
arranging the four dialysis machines on two supply legs, wherein the supply legs are in parallel fluid communication, and wherein at least two of the four dialysis machines are arranged in series on each of the two supply legs.

30. The method of claim 29, further comprising the step of reducing pumping requirements for the parallel arranged dialysis machines as compared to series arranged dialysis machines.

31. A dialysis clinic having reduced fluid flow resistance comprising:
a feeder conduit;
at least two supply legs in parallel fluid arrangement, each supply leg being in fluid communication with the feeder conduit;
at least two dialysis machines respectively fluidly connected to the at least two supply legs; and
a return conduit in fluid communication with the at least two supply legs, whereby
the resistance to fluid flow is reduced as compared to a series arrangement of dialysis machines; and
wherein each supply leg comprises four dialysis machines, including one of the at least two dialysis machines, and wherein the parallel fluid arrangement of all of the dialysis machines is such that the resistance to fluid flow is reduced as compared to a series arrangement of all of the dialysis machines.

* * * * *